US00PP12088P2

(12) United States Plant Patent
Skotak, Jr.

(10) Patent No.: US PP12,088 P2
(45) Date of Patent: Sep. 18, 2001

(54) GUZMANIA PLANT NAMED 'APACHE'

(75) Inventor: Chester Skotak, Jr., Costa Rica (CR)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/419,911

(22) Filed: Oct. 18, 1999

(51) Int. Cl.[7] ..... A01N 5/00

(52) U.S. Cl. ..... Plt./371

(58) Field of Search ..... Plt./371

(56) References Cited

PUBLICATIONS

GTITM UPOVROM Citation for 'Apache' as per QZ PBR 991040; Jul. 19, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Apache' characterized by having a compact growth habit; short and dark-green foliage; red inflorescence with a striking white center at the apex of the inflorescence; and flowers which are not clearly visible when blooming.

1 Drawing Sheet

BACKGROUND OF THE INVENTION

The present invention comprises a new and distinct cultivar of Guzmania plant, hereinafter referred to by the cultivar name 'Apache'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water .

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be form offshoots produced by the plant which may then be rooted. The resulting plantlets are detached from the mother plant and may be potted in a suitable growing mixture. Methods for cultivation and crossing of Guzmania are well known.

'Apache' is a product of a planned breeding program which had the objective of creating new and attractive cultivars with distinctive shapes, sizes and flowering forms.

The new cultivar originated from a hybridization made in a controlled breeding program in Balsa, Costa Rica in 1988. The female parent was an unnamed plant of *Guzmania lingulata* (white form No. 131, unpatented)×*Guzmania wittmackii* (purple form). The male parent was *Guzmania wittmackii* 'Rojo Vivo' (unpatented). 'Apache' was discovered and selected within the progeny of the stated parentage by the inventor, Chester Skotak, Jr., in 1994, in a controlled environment in Balsa, Costa Rica.

'Apache' is characterized by its striking red inflorescence with a white center at the apex of the inflorescence. Asexual reproduction of the new cultivar by tissue culture was performed by the inventor in a controlled environment in 1994, and has demonstrated that the combination of characteristics as herein disclosed for the new cultivar are firmly fixed and reproduces true to type through successive generations of asexual reproduction.

BRIEF DESCRIPTION OF THE INVENTION

The following traits have been repeatedly observed and are determined to be basic characteristics of 'Apache' which in combination distinguish this Guzmania as a new and distinct cultivar:

1. Compact growth habit;
2. Short and dark-green foliage;
3. Red inflorescence with a striking white center at the apex of the inflorescence; and
4. Flowers which are not clearly visible when blooming.

'Apache' has not been observed under all possible environmental conditions. The phenotype of the new cultivar may vary significantly with variations in environment such as temperature, light intensity, and daylength, without any change in genotype.

Of the many commerical cultivars known to the present inventor, the most similar in comparison to 'Apache' is the cultivar 'Grand Prix' (unpatented). The leaf color, flower shape and red color of the inflorescence of 'Apache' are similar to those of the inflorescence of 'Grand Prix'. However, 'Apache' has a more compact growth habit, shorter leaves and a striking white center at the apex of the inflorescence. Plants of 'Apache' differ from plants of 'Rojo Vivo', 'Grand Prix', and the unnamed female parent *Guz-*

*mania wittmackii*, in primary bract color, leaf length and color, and scape length.

BRIEF DESCRIPTION OF THE DRAWING

The accompanying photographic illustration is a perspective view of the inflorescence of a typical 'Apache' plant, with colors being as true as possible with illustrations of this type.

DETAILED BOTANICAL DESCRIPTION

The following observations, measurements and values describe plants grown in Evergem, Belgium, under greenhouse conditions which closely approximate those generally used in horticultural practice. The plant described is approximately 9 withsold. Color references are made to The Royal Horticultural Society (R.H.S.) Colour Chart, except where general colors of ordinary significance are used.

Classification: Commercial: Guzmania c.v. 'Apache'.

Parentage:

*Male parent.*—*Guzmania wittmackii* 'Rojo Vivo'.

*Female parent.*—Unnamed plant of *Guzmania lingulata* (white from No. 131)×*Guzmania wittmackii* (purple form).

Species: Guzmania 'Apache' is [*Guzamania lingulata* (white form No. 131)×*Guzmania wittmackii* (purple form)]×*Guzmania wittmackii* 'Rojo Vivo'.

Propagation: Vegetative, by tissue culture.

Plant:

*Form.*—Funnel-form rosette.

*Height.*—Approximately 50–55 cm when flowering.

*Diameter.*—Approximately 46–60 cm.

*Growth habit.*—Compact.

*Vigor.*—It takes approximately 9 months to produce a finished plant from tissue culture to a 15 cm liner, with a finished plant height of 50 cm (includes plant, pot, and bloom) in a standard greenhouse in Belgium.

Foliage:

*Habit.*—Arcuate spreading, upright at an angle of aproximately 45° and slightly arching from the middle.

*Size.*—Approximately 30–35 cm long and 3–4 cm wide.

*Leaf blades.*—Ligulate, acute to attenuate apex, margin entire, surface glabrous, upright at an angle of 45° and arching slightly from the middle to the top. Dark-green, (RHS 147A) but slightly lighter in color.

*Leaf sheaths.*—Upper surface dark green with red striations, lower surface similar with less pronouced red striations.

*Scape.*—Approximately 50–55 cm long and approximately 1 cm in diameter, green (color varying between RHS 146A and 146B for both upper and lower surfaces.

*Scape bracts.*—Imbricate, 7 scape bracts, acute to attenuate apex, margin entire, surface glabrous, foliaceous, concealing the scape, arcuate spreading, upright at an angle of approximately 30° and very little arching. The leaves gradually become brats towards the top of the inflorescence; green (RHS 147A) with red coloring (RHS 42B) at the base (color designations are for both upper at lower surfaces).

*Leaf blade margin.*—Entire.

*Leaf blade surface texture.*—Glabrous.

*Number of leaves.*—20 to 25.

Inflorescence:

*Habit.*—Spike with approximately 15 spirally arranged bracts.

*Diameter.*—For a plant with a 46 cm diameter (rosette of the leaves), the inflorescence has a 22 cm diameter, when measured 16 cm below the top of the inflorescence; a 15 cm diameter, when measured 5 cm below the top of inflorescence; and 8 cm diameter, when measured at the top of the inflorescence.

*Primary bracts.*—15 primary bracts, elliptic shape, acute to attenuate apex, margin entire. Lowest: Green (RHS 152A) at the base with red (RHS 45C) at the middle and green (RHS 147A) towards the apex (color designations are for both upper and lower surfaces); length 17 cm; width 5 cm at the base. Highest: Green-yellow (RHS 151A) at the base, red (color varying between RHS 45 C AND 45D with white (RHS 159C) at the middle(color designation are for both upper and lower surfaces); length 10 cm; width 4 cm at the base.

*Floral bracts.*—1 floral bract for each flower, elliptic shape, apex cucullate, base sessile, margin entire, closely folded around the flowers, slightly visible, approximately 5 cm long and 1.5 cm wide, white (RHS 158C) with greenish (RHS 151A) base (color designations are for both upper and lower surfaces).

*Flowers.*—Slightly visible during anthesis. Sepals: 3, white (RHS 155B), approximately 3.4 cm long and 1.2 cm wide elliptic shape, apex cucullate; base sessile, margin entire. Petals: 3, white (color varying between RHS 155A and 155B), approximately 1.7 cm long and 0.4 cm wide elliptic shape, apex cucullate, base sessile, margin entire. Pistils: 6, white, approximately 1.4 cm long. Stamens: 6 per flower, white, approximately 1.9 cm long. Style: 1 style with 3 lobed stigma per flower.

*Duration of flowers.*—Individual flowers last for one day and the total duration of flowering is approximately 8–10 weeks with the flowers being slightly visible.

Other significant characteristics: The inflorescence holds its color for approximately 6 months.

Pollen: No known pollen produced.

Fruit: No fruit produced.

Disease pest resistance/susceptibility: No specific resistance or susceptibility observed.

I claim:

1. A new and distinct Guzmania plant named 'Apache', substantially as illustrated and described herein.

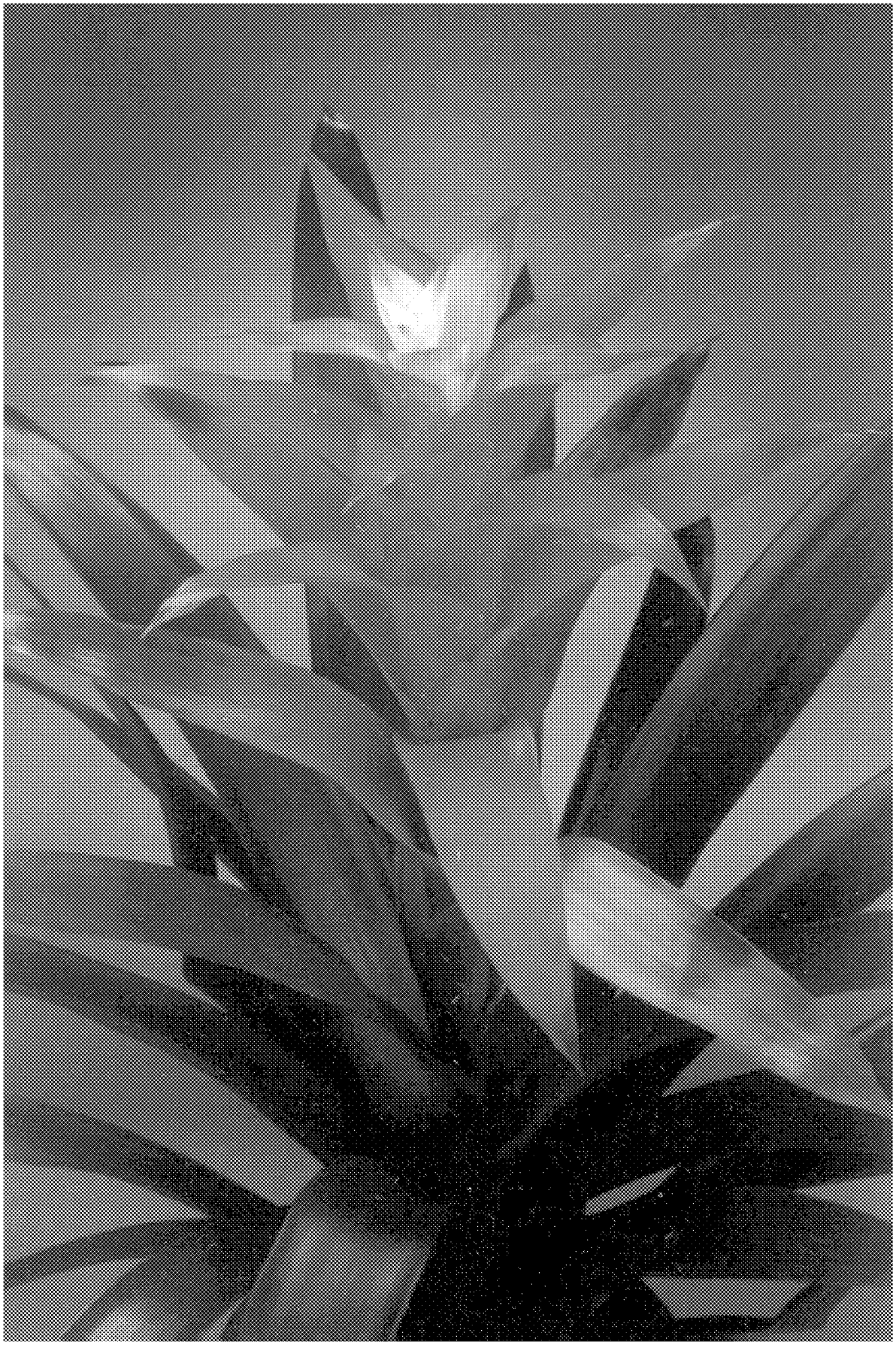

* * * * *